(12) United States Patent
Ono

(10) Patent No.: US 12,263,101 B2
(45) Date of Patent: Apr. 1, 2025

(54) JOINT DEVICE

(71) Applicant: HONDA MOTOR CO., LTD., Tokyo (JP)

(72) Inventor: Hiromi Ono, Saitama (JP)

(73) Assignee: HONDA MOTOR CO., LTD., Tokyo (JP)

(*) Notice: Subject to any disclaimer, the term of this patent is extended or adjusted under 35 U.S.C. 154(b) by 559 days.

(21) Appl. No.: 17/598,870

(22) PCT Filed: Mar. 27, 2020

(86) PCT No.: PCT/JP2020/014002
§ 371 (c)(1),
(2) Date: Sep. 28, 2021

(87) PCT Pub. No.: WO2020/203762
PCT Pub. Date: Oct. 8, 2020

(65) Prior Publication Data
US 2022/0168118 A1 Jun. 2, 2022

(30) Foreign Application Priority Data
Mar. 29, 2019 (JP) .................. 2019-067099

(51) Int. Cl.
*A61F 2/64* (2006.01)
*A61B 5/00* (2006.01)
(Continued)

(52) U.S. Cl.
CPC .............. *A61F 2/64* (2013.01); *A61B 5/4851* (2013.01); *A61F 2/70* (2013.01); *A61F 2002/607* (2013.01); *A61F 2002/6845* (2013.01)

(58) Field of Classification Search
CPC ...... A61F 2/64; A61F 2/70; A61F 2002/6845; A61F 2002/6607; F16D 11/04;
(Continued)

(56) References Cited

U.S. PATENT DOCUMENTS

2004/0102723 A1 5/2004 Horst
2004/0181289 A1 9/2004 Bedard et al.
(Continued)

FOREIGN PATENT DOCUMENTS

DE 324253 C * 8/1920
DE 3227359 A1 2/1983
(Continued)

*Primary Examiner* — Christie Bahena
(74) *Attorney, Agent, or Firm* — CKC & Partners Co., LLC

(57) ABSTRACT

The joint device having a linking unit which links a first member and a second member in a manner allowing relative movement, and having an expansion/contraction device 12 which is connected across the first member 1 and the second member in a manner allowing power transmission and which can modify an angle formed by the first member and the second member around the linking member by expanding and contracting. The expansion/contraction device has a rotary unit which generates rotary power, and a conversion unit which is connected to the rotating unit in a manner allowing power transmission and converts the rotary power generated by the rotary unit into translational motion along a direction of expansion/contraction.

13 Claims, 7 Drawing Sheets

(51) Int. Cl.
*A61F 2/70* (2006.01)
*A61F 2/60* (2006.01)
*A61F 2/68* (2006.01)

(58) Field of Classification Search
CPC .......... F16D 11/10; F16D 11/14; F16D 23/12; F16D 23/123; B25J 9/0006
See application file for complete search history.

(56) References Cited

U.S. PATENT DOCUMENTS

| | | | | |
|---|---|---|---|---|
| 2006/0249315 | A1* | 11/2006 | Herr | A61F 2/6607 623/47 |
| 2007/0123997 | A1* | 5/2007 | Herr | A61F 2/60 602/23 |
| 2010/0191347 | A1* | 7/2010 | Pusch | A61F 2/60 600/595 |
| 2010/0241242 | A1 | 9/2010 | Herr et al. | |
| 2011/0257764 | A1* | 10/2011 | Herr | A61F 2/6607 623/24 |
| 2016/0138679 | A1* | 5/2016 | Tesar | F16H 1/32 475/162 |
| 2016/0158029 | A1 | 6/2016 | Kuiken et al. | |
| 2016/0228265 | A1* | 8/2016 | Herr | A61F 2/70 |
| 2017/0105851 | A1* | 4/2017 | Rouse | A61F 2/6607 |
| 2018/0303636 | A1* | 10/2018 | Pomeroy | F16D 41/08 |

FOREIGN PATENT DOCUMENTS

| | | | | |
|---|---|---|---|---|
| EP | 3539514 | A1 | 9/2019 | |
| JP | H1119105 | A | 1/1999 | |
| JP | 2007512053 | A | 5/2007 | |
| WO | 2005051248 | A1 | 6/2005 | |
| WO | WO-2010088616 | A1 * | 8/2010 | .............. A61F 2/60 |
| WO | WO-2016179281 | A1 * | 11/2016 | .............. A61F 2/64 |
| WO | 2018087997 | A1 | 5/2018 | |

* cited by examiner

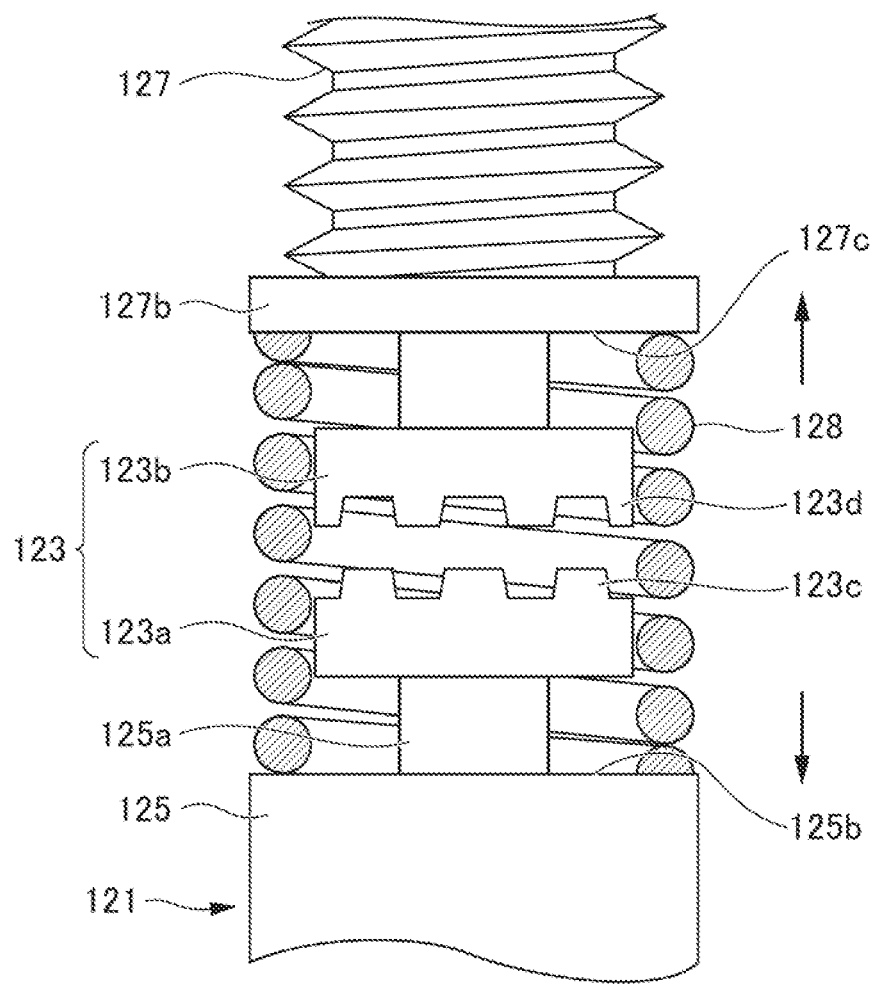

JOINT DEVICE

TECHNICAL FIELD

The present invention relates to a joint device.

BACKGROUND ART

Prostheses (prosthetic arms, prosthetic legs) have been known as joint devices including two members that are relatively movably linked with each other. For example, a prosthetic leg (transfemoral prosthesis) attachable to a femoral region of a lower extremity amputated at a position proximal to the knee joint is a type of knee joint device that includes an above-knee member and a below-knee member linked with each other such that the members can rotationally move relative to each other around a linking unit corresponding to the knee.

Such a prosthetic leg has a yielding function of bending, at a moderate degree of hydraulic resistance, around the linking unit corresponding to the knee joint. This function can prevent the knee part of the prosthetic leg from abruptly bending upon application of a load. This function also enables a wearer to descend a staircase by swinging the prosthetic leg and his/her ordinary leg forward in turn.

A known prosthetic leg is configured such that based on detected information from a sensor that detects contractile motion of muscles and is provided at a socket where a stump is received, a degree of throttling of a variable valve of a hydraulic cylinder is controlled, so that resistance to bending and straightening a knee joint is adjusted (see, for example, Patent Document 1).

Patent Document 1: Japanese Unexamined Patent Application, Publication No. H11-19105

DISCLOSURE OF THE INVENTION

Problems to be Solved by the Invention

However, while being capable of bending the knee part by the yielding function, the conventional prosthetic leg cannot straighten the knee part without being swung forward. That is, with the conventional prosthetic leg, the wearer cannot straighten the knee part while bracing the prosthetic leg with application of a load to the prosthetic leg and while moving his/her body upward. Therefore, the conventional prosthetic leg does not allow the wearer to ascend a staircase with a nearly normal gait.

In view of the foregoing background, it is an object of the present invention to provide a joint device that can be straightened from a bent state, while a load is applied to the joint device.

Means for Solving the Problems

A first aspect of the present invention is directed to a joint device (e.g., a prosthetic leg 10 to be described later) including: a linking unit (e.g., a knee joint mechanism 3 to be described later) that links a first member (e.g., a below-knee member 1 to be described later) with a second member (e.g., an above-knee member 2 to be described later) such that the first and second members are movable relative to each other; and an extension/contraction device (e.g., an extension/contraction device 12 to be described later) that is connected between the first member and the second member in a manner allowing power transmission, and is capable of varying an angle formed by the first member and the second member around the linking unit, by extending and contracting. The extension/contraction device includes a rotary unit (e.g., a rotary unit 121 to be described later) that is configured to generate a rotational power, and a conversion unit (e.g., a conversion unit 122 to be described later) that is connected to the rotary unit in a manner allowing power transmission and is configured to convert the rotational power generated by the rotary unit into translational motion in an extension/contraction direction.

The first aspect can provide the joint device that can be straightened from a state where the first and second members form a bend, while a load is applied to the joint device.

A second aspect of the present invention is an embodiment of the first aspect. In the joint device of the second aspect, the rotary unit may include a rotating machine (e.g., a rotating machine 124) that generates a rotational power upon supply of electric power.

According to the second aspect, the rotational power of the rotary unit can be generated by means of the rotational power of the rotating machine.

A third aspect of the present invention is an embodiment of the second aspect. The joint device of the third aspect may further include a control unit (e.g., a control unit 17 to be described later) that controls the rotational power of the rotating machine.

According to the third aspect, the rotational power of the rotating machine can be suitably controlled by the control unit.

A fourth aspect of the present invention is an embodiment of the third aspect. In the joint device of the fourth aspect, the control unit may be configured to control the rotating machine such that when an external force acting in a contraction direction is applied to the extension/contraction device, the rotating machine generates a rotational power acting in a direction, the rotational power being converted by the conversion unit into translational motion in an extension direction.

According to the fourth aspect, while waste of power consumption and heat generation by the rotating machine is reduced, the rotating machine can be controlled to generate the rotational power in the direction, which is converted by the conversion unit into the translational motion in the extension direction.

A fifth aspect of the present invention is an embodiment of any one of the first to fourth aspects. In the joint device of the fifth aspect, in a state where the joint device is attached to a wearer's body such that the first member is positioned toward a distal end and is more distant than the second member from the wearer's body, the rotary unit may be more distant than the conversion unit from the second member.

According to the fifth aspect, since the rotary unit is heavier than the conversion unit composed of an outer cylinder and a spindle, when the wearer walks in a normal manner by swinging the prosthetic leg and his/her ordinary leg forward in turn, inertia caused by the weight of the rotary unit can be effectively used. Further since a center of gravity of the prosthetic leg is at a low position, the posture of the wearer is stabilized when he/she is in a standing position.

A sixth aspect of the present invention is an embodiment of any one of the first to fifth aspects. In the joint device of the sixth aspect, the extension/contraction device may further include, between the rotary unit and the conversion unit, a connection/disconnection unit (e.g., a clutch unit 123 to be described later) that is capable of connecting and disconnecting power transmission from the rotary unit to the conversion unit.

According to the sixth aspect, the rotational power of the rotary unit can be interrupted to be prevented from being transmitted to the conversion unit, thereby inhibiting application of an unnecessary load to the rotary unit.

A seventh aspect of the present invention is an embodiment of the sixth aspect. In the joint device of the seventh aspect, the connection/disconnection unit may include a first connection/disconnection member (e.g., a first engagement element 123a to be described later) coupled to a side of the rotary unit and a second connection/disconnection member (e.g., a second engagement element 123b to be described later) coupled to a side of the conversion unit, and may further include a first urging part (e.g., a spring 128 to be described later) that applies an urging force in a direction in which the first and second connection/disconnection members are constantly spaced apart from each other.

According to the seventh aspect, when an external force acting in a direction in which the rotary unit and the conversion unit are arranged becomes less intense than the urging force of the first urging part, the connection/disconnection unit can be automatically brought into a disconnected state.

An eighth aspect of the present invention is an embodiment of any one of the first to seventh aspects. In the joint device of the eighth aspect, the rotary unit may further include a transmission (e.g., a transmission 125 to be described later).

The eighth aspect makes it possible to increase a degree of freedom in selection of a drive power generator of the rotary unit.

A ninth aspect of the present invention is an embodiment of any one of the first to eighth aspects. In the ninth aspect, the joint device may further include an adjustment unit (e.g., a rotary damper 32 to be described later) that adjusts a movement of the linking unit.

The ninth aspect makes it possible to adjust a relative rotational movement of the first and second members, thereby making it less likely for an abrupt bend to occur between the first and second members.

A tenth aspect of the present invention is an embodiment of any one of the first to ninth aspects. In the joint device of the tenth aspect, the extension/contraction device may further include a second urging part (e.g., the spring 128 to be described later) that urges the rotary body in one rotation direction.

According to the tenth aspect, the rotary body is urged in the one direction by the second urging part, thereby making it possible to rotate the rotary body in the one direction, without using the rotational power of the rotary unit.

An eleventh aspect of the present invention is an embodiment of any one of the first to tenth aspects. In the eleventh aspect, the joint device may further include a first acquisition unit (e.g., a six-axis force sensor 14 to be described later) that acquires information regarding an external force acting in the contraction direction and applied to the extension/contraction device.

The eleventh aspect makes it possible to estimate a state of the joint device, based on the external force acting in the contraction direction and applied to the extension/contraction device.

A twelfth aspect of the present invention is an embodiment of any one of the first to eleventh aspects. In the twelfth aspect, the joint device may further include a second acquisition unit (e.g., a six-axis motion sensor 15 to be described later) that acquires information regarding an acceleration of the first member.

The twelfth aspect makes it possible to estimate a state of the joint device from the acceleration of the first member.

A thirteenth aspect of the present invention is an embodiment of any one of the first to twelfth aspects. In the thirteenth aspect, the joint device may further include a third acquisition unit (e.g., a knee joint angle sensor 16) that acquires information regarding the angle formed by the first member and the second member.

The thirteenth aspect makes it possible to estimate a state of the joint device from the angle formed by the first member and the second member.

A fourteenth aspect of the present invention is an embodiment of any one of the first to thirteenth aspects. In the fourteenth aspect, the joint device may further include a battery (e.g., a battery 13 to be described later) that supplies the rotary unit with electric power for generation of the rotational power.

The fourteenth aspect makes it possible for the rotary unit in the joint device to generate the rotational power, without external supply of electric power.

A fifteenth aspect of the present invention is an embodiment of any one of the first to fourteenth aspects. In the fifteenth aspect, the joint device may be attachable to a lower extremity of a wearer's body.

The fifteenth aspect provides the joint device attachable to the lower extremity of the wearer's body.

A sixteenth aspect of the present invention is an embodiment of the fifteenth aspect. In the sixteenth aspect, the joint device may be attachable to a part to serve as a knee joint of the lower extremity.

The sixteenth aspect provides the knee joint device attachable to the lower extremity of the wearer's body.

Effects of the Invention

The present invention provides a joint device that can be straightened from a bent state, while a load is applied to the joint device.

BRIEF DESCRIPTION OF THE DRAWINGS

FIG. 2 is an enlarged diagram schematically illustrating an embodiment of a clutch unit provided to an extension/contraction device;

PREFERRED MODE FOR CARRYING OUT THE INVENTION

An embodiment of a joint device according to the present invention will be described in detail with reference to the drawings. The present specification describes, as an example of the joint device, a transfemoral prosthesis (hereinafter referred to as the prosthetic leg) that is a type of knee joint device attachable to a part to serve as a knee joint and located in a femoral region of a lower extremity.

(Overall Configuration of Prosthetic Leg)

Figure 1:
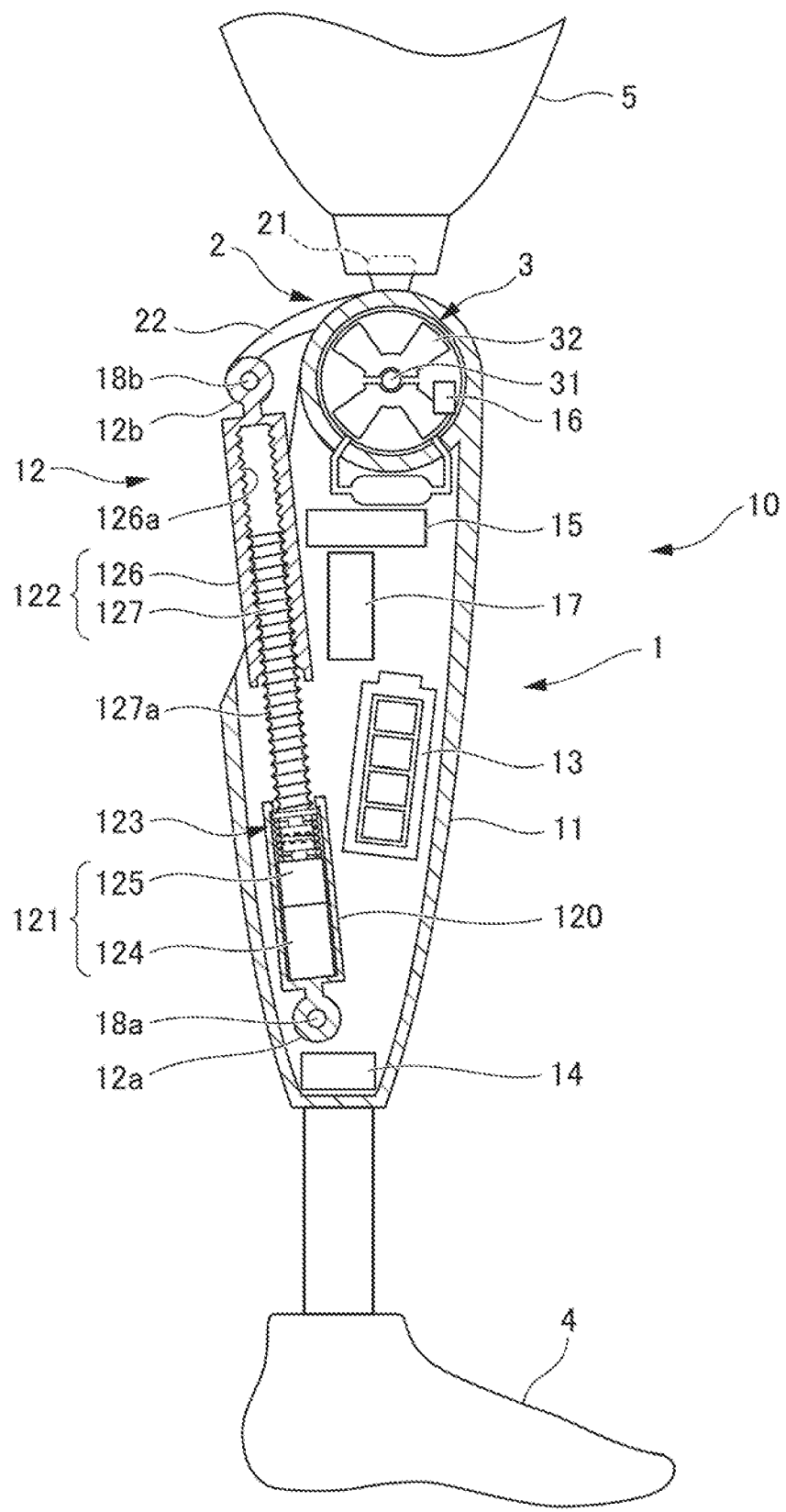
FIG. 1 is a side view illustrating principal components of a prosthetic leg in cross section.

FIG. 1 is a side view illustrating principal components of the prosthetic leg in cross section. As illustrated in FIG. 1, the prosthetic leg 10 has a below-knee member 1 and an above-knee member 2. The below-knee member 1 is coupled to the above-knee member 2 via a knee joint mechanism 3. The below-knee member 1 corresponds to a "first member" of the present invention. The above-knee member 2 corresponds to a "second member" of the present invention. The below-knee member 1 has a lower end coupled to a foot part 4. The above-knee member 2 is disposed at an upper end of the below-knee member 1. The above-knee member 2 has an upper end coupled to a socket 5 that is configured to receive a stump of a femoral region of a lower extremity of a wearer's body (human body; not illustrated).

Note that directions with respect to the prosthetic leg 10 will be described based on a state in which the wearer's body having the prosthetic leg 10 attached thereto is in a standing position. Specifically, "above/upper/upward" and "below/lower/downward" with respect to the prosthetic leg 10 correspond to "above/upper/upward" and "below/lower/downward" with respect to the wearer's body in the standing position, and correspond to upward and downward directions in FIG. 1. "Front/forward" and "rear/rearward" (a front face and a rear face) with respect to the prosthetic leg 10 correspond to "front/forward" and "rear/rearward" (a front face and a rear face) with respect to the wearer's body in the standing position, and correspond to right and left directions in FIG. 1.

(Knee Joint Mechanism)

The knee joint mechanism 3 corresponds to the knee of the prosthetic leg 10, and links the below-knee member 1 with the above-knee member 2 such that the below-knee member 1 and the above-knee member 2 can rotationally move relative to each other around a centered pivot shaft 31 in the forward and rearward directions of the prosthetic leg 10 (in clockwise and counterclockwise directions in FIG. 1). The knee joint mechanism 3 corresponds to a "linking unit" of the present invention.

In the following, the relative rotational movement of the below-knee member 1 and the above-knee member 2 around the pivot shaft 31 of the knee joint mechanism 3 will be described based on a case where the below-knee member 1 is stationary while the above-knee member 2 rotationally moves in the forward direction (clockwise direction) or the rearward direction (counterclockwise direction) in FIG. 1.

The knee joint mechanism 3 of the present embodiment includes a rotary damper 32 configured to adjust the rotational movement of the knee joint mechanism 3. The rotary damper 32 is rotatable around the pivot shaft 31 of the knee joint mechanism 3, and adjusts the relative rotational movement of the below-knee member 1 and the above-knee member 2 around the pivot shaft 31, into a movement at a moderate degree of hydraulic resistance. The prosthetic leg 10 of the present embodiment includes the rotary damper 32 provided to the knee joint mechanism 3, and thereby performs a function of preventing abrupt knee bending and a yielding function. The rotary damper 32 corresponds to an "adjustment unit" of the present invention.

(Above-Knee Member)

The above-knee member 2 is mounted such that it can rotationally move around the pivot shaft 31 of the knee joint mechanism 3, in the forward and rearward directions of the prosthetic leg 10. The above-knee member 2 has a socket-coupling projection 21 having an upper end couplable to the socket 5, and an arm part 22 extending from a portion directly under the socket-coupling projection 21 in the rearward direction with respect to the prosthetic leg 10, specifically, in the rearward direction with respect to the knee joint mechanism 3.

(Below-Knee Member)

The below-knee member 1 corresponds to the crus of the prosthetic leg 10, and forms a main portion of the prosthetic leg 10. The below-knee member 1 of the present embodiment has, in a frame 11 corresponding to the lower leg of the prosthetic leg 10, an extension/contraction device 12, a battery 13, a six-axis force sensor 14, and a six-axis motion sensor 15, a knee joint angle sensor 16, and a control unit 17. The knee joint mechanism 3 is disposed in an upper end portion of the frame 11. Note that wires electrically connecting the components to each other are omitted from FIG. 1.

A. Extension/Contraction Device

The extension/contraction device 12 is disposed in a rear portion of an interior of the frame 11 and is extendible and contractable in the upward/downward direction. The extension/contraction device 12 has a lower end attached to a first pivot 18a disposed in proximity to a lower end of the interior of the frame 11 by means of an attachment part 12a such that the lower end of the extension/contraction device 12 is pivotable in the forward/rearward direction of the prosthetic leg 10. On the other hand, the extension/contraction device 12 has an upper end exposed to the outside from the frame 11 and attached to a second pivot 18b disposed at a leading end of the arm part 22 of the above-knee member 2 by means of an attachment part 12b such that the upper end of the extension/contraction device 12 is pivotable in the forward/rearward direction of the prosthetic leg 10. Thus, the extension/contraction device 12 is disposed between the below-knee member 1 and the above-knee member 2. When the extension/contraction device 12 extends or contracts, the arm part 22 of the above-knee member 2 moves upward or downward, thereby causing the above-knee member 2 to pivot around the pivot shaft 31 of the knee joint mechanism 3. In this way, an angle formed by the below-knee member 1 and the above-knee member 2 is varied.

The extension/contraction device 12 of the present embodiment has a rotary unit 121 that generates a rotational power, and a conversion unit 122 that converts the rotational power generated by the rotary unit 121 into translational motion in an extension/contraction direction. A clutch unit 123 capable of connecting and disconnecting power transmission from the rotary unit 121 to the conversion unit 122 is further provided between the rotary unit 121 and the conversion unit 122.

a1. Rotary Unit

The rotary unit 121 has a rotating machine 124 functioning as a drive power generator. The rotating machine 124 is housed in a cylindrical housing 120 having an open top end, and generates the rotational power upon supply of electric power from the battery 13. The housing 120 is pivotably attached to the first pivot 18a disposed in the lower end portion of the interior of the frame 11 by means of the attachment part 12a. The housing 120 is disposed rearwardly obliquely from the first pivot 18a. Specific examples of the rotating machine 124 are not particularly limited, but may include a stepping motor, a DC motor, etc. The rotating machine 124 is housed in a lowermost portion of an interior of the housing 120, while having an output shaft (not illustrated) facing upward.

The rotary unit 121 of the present embodiment further has a transmission 125 that is housed in the housing 120, together with the rotating machine 124. The transmission 125 is coupled to the output shaft of the rotating machine 124, and outputs the rotational power while varying a ratio of a rotational speed of the output shaft. This configuration makes it possible to increase a degree of freedom in selection of the rotating machine 124 to be used in the rotary unit 121. As the transmission 125, a speed reducing gear or a speed increasing gear can be used. In the case of using the speed reducing gear, the rotational power of the rotating machine 124 can be converted into a rotational power with a high torque. On the other hand, in the case of using the speed increasing gear, the rotational power of the rotating machine 124 can be converted into a high-speed rotational power.

a2. Conversion Unit

The conversion unit 122 has an outer cylinder 126 having an open bottom end, and a spindle 127 extending from the outer cylinder 126 to the housing 120 and having a rod shape.

The outer cylinder 126 is pivotably attached to the second pivot 18b disposed on the arm part 22 of the above-knee member 2 by means of the attachment part 12b, and extends from the second pivot 18b toward the housing 120 so as to be inserted in the frame 11. The outer cylinder 126 has, on an inner peripheral surface thereof, a female thread 126a helically extending along substantially the entire axial length of the outer cylinder 126.

The spindle 127 has, on an outer peripheral surface thereof, a male thread 127a extending along substantially the entire axial length of the spindle 127, and engageable with the female thread 126a in the outer cylinder 126. The spindle 127 has an upper end portion engaged with the female thread 126a in the outer cylinder 126, whereby the upper end portion of the spindle 127 can rotate around an axis thereof, while being received in the outer cylinder 126. On the other hand, the spindle 127 has a lower end portion attached to an upper end of the interior of the housing 120 such that the lower end portion is rotatable around its axis, but is allowed to move only by a distance within a range of a connection/disconnection movement of the clutch unit 123, which will be described later. In the housing 120, the spindle 127 is arranged to be able to transmit the rotational power of the rotating machine 124. The spindle 127 corresponds to a "rotary body" of the present invention.

The spindle 127 rotates around its axis when the rotational power of the rotating machine 124 in the housing 120 is transmitted to the spindle 127. Rotation of the spindle 127 moves the outer cylinder 126, which is threaded on the spindle 127, upward or downward in the axial direction of the spindle 127. As a result, a distance by which the outer cylinder 126 is spaced apart from the housing 120 varies, and the entire length of the extension/contraction device 12 increases or decreases. Specifically, the spindle 127 and the outer cylinder 126 forming the conversion unit 122 are configured to convert the rotational power generated by the rotary unit 121 into translational motion in the extension/contraction direction. When extending or contracting, the extension/contraction device 12 moves the arm part 22, to which the outer cylinder 126 is attached by means of the second pivot 18b, upward or downward, and causes the above-knee member 2 to pivot around the pivot shaft 31 in the forward or rearward direction of the prosthetic leg 10, thereby varying the angle formed by the below-knee member 1 and the above-knee member 2.

The extension/contraction device 12 of the present embodiment is configured to move the outer cylinder 126 in an extension direction when the rotational power from the rotary unit 121 rotates the spindle 127 around its axis in a direction (forward rotation) on one hand, and is configured to move, in a contraction direction, the outer cylinder 126 that has been moved in the extension direction when the rotational power from the rotary unit 121 rotates the spindle 127 around its axis in a direction opposite to the above direction (backward rotation) on the other hand. A configuration causing the spindle 127 to rotate backward around its axis will be described later.

In the frame 11, the conversion unit 122 and the rotary unit 121 of the extension/contraction device 12 of the present embodiment are arranged such that the rotary unit 121 is more distant from the above-knee member 2 (and closer to the foot part 4 of the prosthetic leg 10) than the conversion unit 122 is. In other words, the outer cylinder 126 and the housing 120 including the rotary unit 121 are arranged in an upper portion and a lower portion of the prosthetic leg 10, respectively, while having the spindle 127 interposed therebetween. Since the rotary unit 121 is heavier than the conversion unit 122 composed of the outer cylinder 126 and the spindle 127, when a wearer of the prosthetic leg 10 walks in a normal manner by swinging the prosthetic leg 10 and his/her ordinary leg forward in turn, inertia caused by the weight of the rotary unit 121 can be effectively used. Further since a center of gravity of the prosthetic leg 10 is at a low position, the posture of the wearer is stabilized when he/she is in the standing position.

a3. Clutch Unit

The clutch unit 123 has a first engagement element 123a coupled to a side of the rotary unit 121, and a second engagement element 123b coupled to a side of the conversion unit 122, and is disposed in the housing 120 of the extension/contraction device 12 such that clutch unit 123 can connect and disconnect the power transmission from the rotary unit 121 to the conversion unit 122. The clutch unit 123 corresponds to a "connection/disconnection unit" of the present invention. The first engagement element 123a corresponds to a "first connection/disconnection member" of the present invention. The second engagement element 123b corresponds to a "second connection/disconnection member" of the present invention.

FIG. 2 is an enlarged diagram schematically illustrating an embodiment of the clutch unit 123 provided to the extension/contraction device 12. The first engagement element 123a is provided on an output shaft 125a of the transmission 125 forming part of the rotary unit 121, and projects upward toward the spindle 127. On the other hand, the second engagement element 123b is provided on a lower end portion 127b of the spindle 127, and projects downward toward the transmission 125. The first engagement element 123a has a surface facing a surface of the second engagement element 123b. The surface of the first engagement element 123a and the surface of the second engagement element 123b have pawls 123c and pawls 123d, respectively, which can be meshed with each other.

Figure 3A:
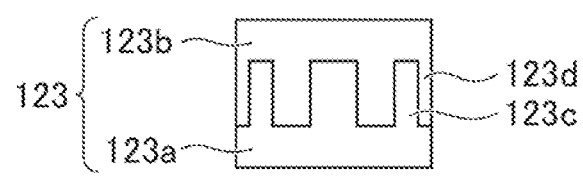
FIG. 3A is an enlarged diagram schematically illustrating a clutch unit in a meshed state, the clutch unit including pawls having a rectangular shape in cross section.
Figure 3B:
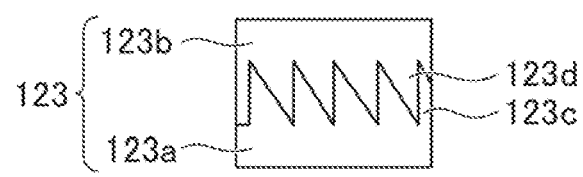
FIG. 3B is an enlarged diagram schematically illustrating a clutch unit in a meshed state, the clutch unit including pawls having a sawtooth shape in cross section.

The pawls 123c of the first engagement element 123a and the pawls 123d of the second engagement element 123b may have any specific shape, as long as the rotational power of the rotary unit 121 can be transmitted to the spindle 127 when the pawls 123c and 123d are meshed with each other. The pawls 123c and 123d may have a trapezoidal shape in cross section as illustrated in FIG. 2, or a rectangular shape in cross section as illustrated in FIG. 3A. Alternatively, the pawls 123c and 123d may have a sawtooth shape in cross section as illustrated in FIG. 3B.

The transmission 125 has an output-side end surface 125b and the spindle 127 has a lower end surface 127c. A spring 128 is disposed between the end surfaces 125b and 127c. The spring 128 is constituted by an appropriate elastic member, such as a coil spring, and accommodates therein the first engagement element 123a and the second engagement element 123b. The spring 128 is configured to constantly apply an urging force to the output-side end surface 125b of the transmission 125 and the spindle 127 in a direction in which the first engagement element 123a and the second engagement element 123b are spaced apart from each other and the pawls 123c and 123d are unmeshed from each other. The spring 128 is also configured to contract in the axial direction when an axial load having a predetermined intensity acts on the spindle 127 such that the pawls 123c of the first engagement element 123a and the pawls 123d of the second engagement element 123b can be meshed with each other. When the spring 128 deforms to cause the first engagement element 123a to mesh with the second engagement element 123b, the rotational power generated by the rotary unit 121 is transmitted via the transmission 125 to the spindle 127. The spring 128 corresponds to a "first urging part" of the present invention.

The urging force of the spring 128 of the present embodiment is set such that when the above-knee member 2 is caused to pivot rearward (in the counterclockwise direction) around the pivot shaft 31 and an axial load is applied to the extension/contraction device 12, the spring 128 contracts in the axial direction, thereby causing the first engagement element 123a and the second engagement element 123b to mesh with each other.

As illustrated in FIG. 2, the spring 128 of the present embodiment is constituted by a coil spring. In this case, the spring 128 may have one end fixed to the output-side end surface 125b of the transmission 125, and the other end fixed to the lower end surface 127c of the spindle 127. This configuration allows the spring 128 to function also as an urging member configured to urge the spindle 127 in one rotation direction. Specifically, when the spring 128 contracts in the axial direction to cause the first engagement element 123a to mesh with the second engagement element 123b, the rotational power of the rotary unit 121 is transmitted via the clutch unit 123 to the spindle 127, so that the spindle 127 rotates in the forward direction while twisting the spring 128 against the urging force acting in the rotation direction. When the application of the load to the extension/contraction device 12 is stopped, the spring 128 elastically resumes its original shape in the axial direction, so that the first engagement element 123a becomes unmeshed from the second engagement element 123b and the clutch unit 123 is brought into a disconnected state. In this way, the spring 128 elastically resumes, by the urging force, its original shape from the twisted state around the axis, and rotates the spindle 127 backward. Thus, the spring 128 having the above configuration corresponds to a "second urging part" of the present invention.

B. Battery

The battery 13 is constituted by, for example, a lithium-ion secondary battery capable of charging and discharging, and is disposed forward of the extension/contraction device 12 in the frame 11. The battery 13 is connected to be able to supply the rotating machine 124 of the rotary unit 121 with electric power, and to be able to supply the six-axis force sensor 14, the six-axis motion sensor 15, the knee joint angle sensor 16, and the control unit 17 with electric power required for driving the respective components. In general, the battery 13 is detachably incorporated in the frame 11. However, the battery 13 may be chargeable by way of contact or non-contact (wired or wireless) charging from an external device, while remaining in the frame 11.

When a rotary force from the spindle 127 acts on the rotating machine 124 when it is not in operation, the rotating machine 124 functions as a generator to convert the rotary force into electric power. The battery 13 of the present embodiment may be configured to be able to regenerate the electric power provided through the conversion by the rotating machine 124.

C. Six-Axis Force Sensor

The six-axis force sensor 14 is capable of detecting three-axis load and three-axis moment of the prosthetic leg 10 in the forward/rearward direction, the right/left direction, and the upward/downward direction, and is disposed in a lower end portion of the interior of the frame 11. The six-axis force sensor 14 acquires information regarding an external force acting in a contraction direction and applied to the extension/contraction device 12, based on a detection signal that is detected when the foot part 4 of the prosthetic leg 10 attached to a wearer's body contacts with the ground or the like. The detection result is transmitted to the control unit 17. The six-axis force sensor 14 corresponds to a "first acquisition unit" of the present invention.

D. Six-Axis Motion Sensor

The six-axis motion sensor 15 is capable of detecting three-axis acceleration and three-axis angular acceleration of the prosthetic leg 10 in the forward/rearward direction, the right/left direction, and the upward/downward direction, and is disposed directly under the knee joint mechanism 3, in an upper portion of the interior of the frame 11. The six-axis motion sensor 15 acquires information regarding an acceleration acting on the prosthetic leg 10, based on a detection signal that is detected when the prosthetic leg 10 attached to the wearer's body moves. The detection result is transmitted to the control unit 17. The six-axis motion sensor 15 corresponds to a "second acquisition unit" of the present invention.

E. Knee Joint Angle Sensor

The knee joint angle sensor 16 is a sensor capable of detecting angle information, such as a rotary encoder, and is provided at the knee joint mechanism 3. The knee joint angle sensor 16 acquires information regarding the angle that is formed by the below-knee member 1 and the above-knee member 2, as a consequence of a relative rotational movement of the members. The detection result is transmitted to the control unit 17. The knee joint angle sensor 16 corresponds to a "third acquisition unit" of the present invention.

F. Control Unit

The control unit 17 is constituted by, for example, an electronic control unit (ECU), and is configured to control the rotational power of the rotating machine 124. Specifically, the control unit 17 estimates a state of the prosthetic leg 10 based on the detection results transmitted from the six-axis force sensor 14, the six-axis motion sensor 15, and the knee joint angle sensor 16, and outputs a control signal to the rotating machine 124 to cause the rotating machine 124 to generate a rotational power suitable for the state of the prosthetic leg 10.

(Movements of Prosthetic Leg)

Figure 4:
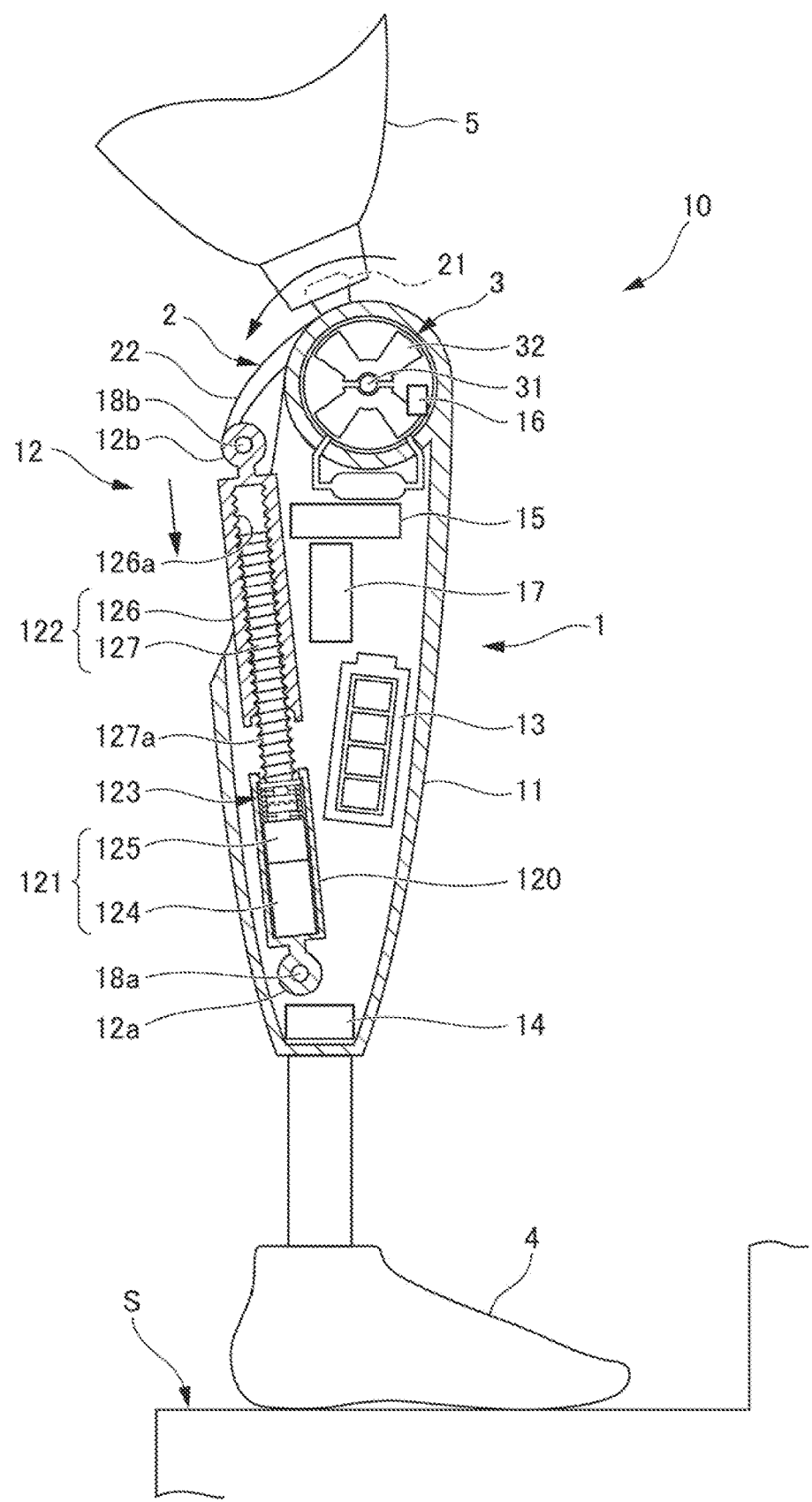
FIG. 4 is a diagram illustrating a prosthetic leg in a stair-ascending state, the prosthetic leg being in contact with a step of a staircase.
Figure 5:
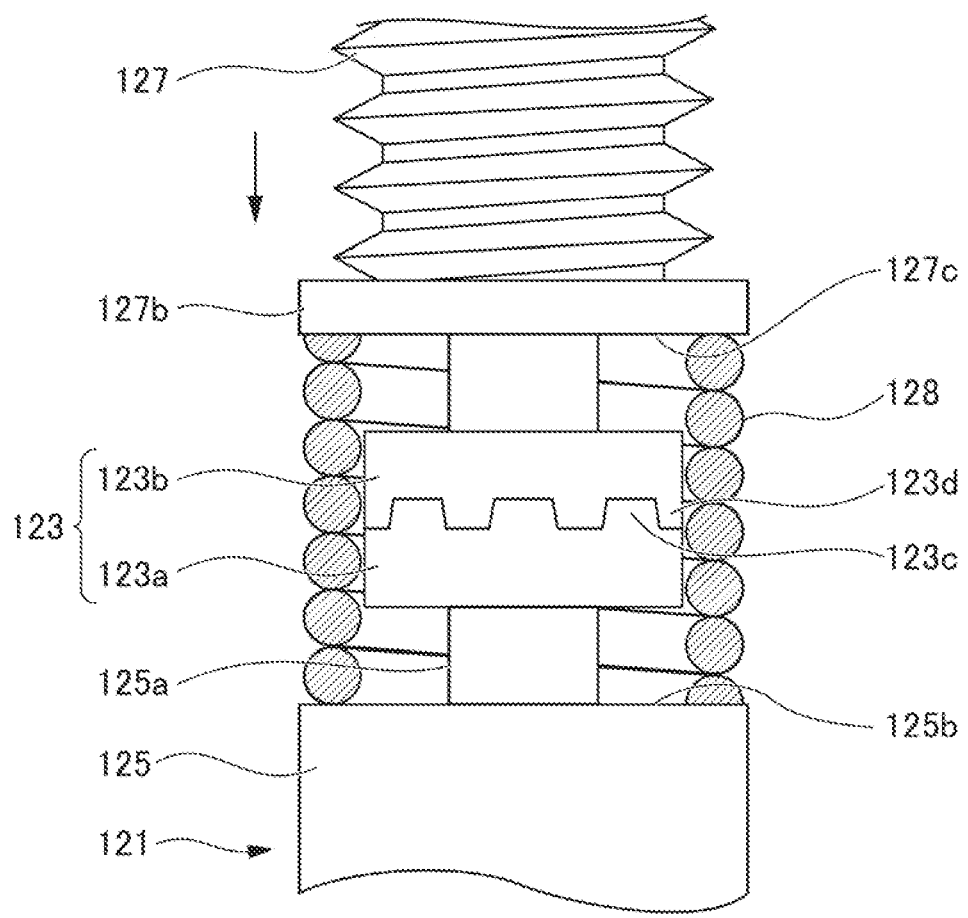
FIG. 5 is an enlarged diagram schematically illustrating a clutch unit provided to an extension/contraction device, the clutch unit being in a meshed state.
Figure 6:
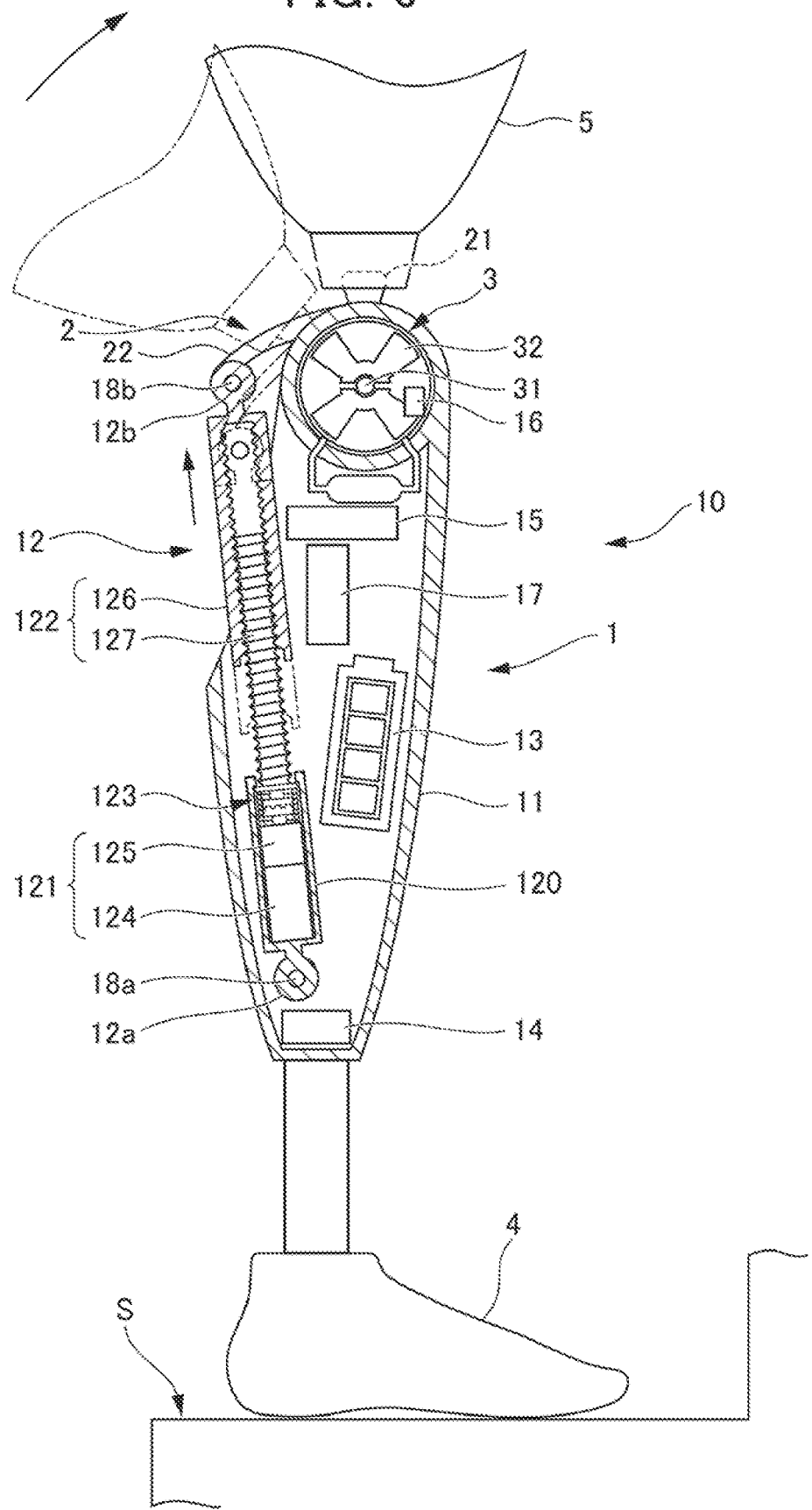
FIG. 6 is a diagram illustrating a prosthetic leg in a state where an extension/contraction device is extended.
Figure 7:
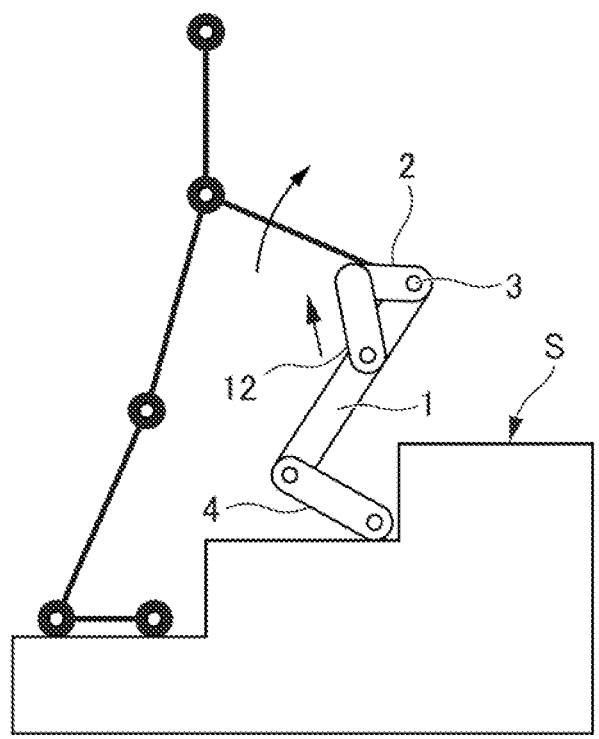
FIG. 7 is a diagram schematically illustrating a wearer's body having the prosthetic leg attached thereto and ascending a staircase.

Next, movements of the prosthetic leg 10 will be specifically described with reference to FIGS. 1 and 4 to 7. FIG. 4 is a diagram illustrating the prosthetic leg in a stair-ascending state, the prosthetic leg being in contact with a step of a staircase. FIG. 5 is an enlarged diagram schematically illustrating the clutch unit provided to the extension/contraction device, the clutch unit being in a meshed state. FIG. 6 is a diagram illustrating the prosthetic leg in a state where the extension/contraction device is extended. FIG. 7 is a diagram schematically illustrating the wearer's body having the prosthetic leg attached thereto and ascending a staircase.

First, reference is made to FIG. 1 illustrating prosthetic leg 10 in the standing position. In this position, a femoral region of a lower extremity of the wearer's body (not illustrated) is applying a load in a substantially vertical direction to the prosthetic leg 10 via the socket 5, in the direction from the above-knee member 2 to the foot part 4. At this time, the above-knee member 2 is not caused to pivot rearwardly, and an external force (body weight) in the contraction direction does not act on the extension/contraction device 12. Therefore, the spring 128 exerts an urging force to space the spindle 127 and the rotary unit 121 of the extension/contraction device 12 apart from each other, whereby the first engagement element 123a and the second engagement element 123b of the clutch unit 123 is spaced apart from each other. Accordingly, even when the rotating machine 124 is driven and rotated, the rotational power of the rotating machine 124 is not allowed to act on the spindle 127, and the extension/contraction device 12 is prevented from operating. Since the rotating machine 124 does not receive any load, the rotating machine 124 is inhibited from generating heat.

At this time, the control unit 17 estimates that the prosthetic leg 10 is in the standing position, based on the detection results transmitted from the six-axis force sensor 14, the six-axis motion sensor 15, and the knee joint angle sensor 16, and performs control such that the rotating machine 124 stops or is inhibited from generating an unnecessary rotational power. This configuration reduces waste of power consumption.

When the prosthetic leg 10 transitions to flat-ground walking (a walking mode) and a load is applied to a heel area of the prosthetic leg 10 in a stance phase, the above-knee member 2 is caused to pivot rearward (in the counterclockwise direction) around the pivot shaft 31 of the knee joint mechanism 3. The pivotal movement of the above-knee member 2 moves the arm part 22 downward, and accordingly, an external force acting in the contraction direction is applied to the outer cylinder 126 of the extension/contraction device 12. Consequently, the outer cylinder 126 presses the spindle 127 in the axial direction toward the rotary unit 121, thereby causing the spring 128 disposed between the transmission 125 of the rotary unit 121 and the spindle 127 to contract in the axial direction, so that the first engagement element 123a and the second engagement element 123b of the clutch unit 123 are meshed with each other. Concurrently with this, the rotary damper 32 of the knee joint mechanism 3 adjusts the pivotal movement of the above-knee member 2 into a movement at a moderate degree of hydraulic resistance, thereby preventing abrupt knee bending. The external force acting in the contraction direction and applied at this time to the extension/contraction device 12 is a force (load) greater than a rotational torque of the rotating machine 124. Therefore, the rotary unit 121 cannot rotate the spindle 127 in the forward direction, so that the extension/contraction device 12 does not extend.

In the walking mode, for example, when the prosthetic leg 10 transitions from the stance phase to a swing phase and the application of the external force acting in the contraction direction to the extension/contraction device 12 is stopped, the spring 128 elastically resumes its original shape in the axial direction to cause the spindle 127 to move the outer cylinder 126 upward to its original position, so that the above-knee member 2 is caused to pivot forward (in the clockwise direction) around the pivot shaft 31. As a result, the prosthetic leg 10 returns to the standing position and becomes ready for next application of a load.

Next, a case where the wearer with the prosthetic leg 10 ascends a staircase S will be described. As illustrated in FIG. 4, when the wearer moves his/her femoral region upward, the prosthetic leg 10 is raised above his/her normal foot and then contacts with an upper step of the staircase S. At this time, the above-knee member 2 is caused to pivot rearward (in the counterclockwise direction) around the pivot shaft 31 of the knee joint mechanism 3, thereby moving the leading end of the arm part 22 downward. That is, the prosthetic leg 10 is brought into a state where the knee is bent. When the downward movement of the arm part 22 applies an external force acting in the contraction direction to the extension/contraction device 12, the outer cylinder 126 presses the spindle 127 in the axial direction toward the rotary unit 121, thereby causing the spring 128 disposed between the transmission 125 of the rotary unit 121 and the spindle 127 to contract in the axial direction, so that the first engagement element 123a and the second engagement element 123b of the clutch unit 123 are meshed with each other.

For example, an acceleration at which the prosthetic leg 10 is raised above a step of a staircase S and is brought into contact with the step, and a load applied to the prosthetic leg 10 at the time of contacting with the step are detected by the six-axis force sensor 14, the six-axis motion sensor 15, and the knee joint angle sensor 16, whereby the control unit 17 estimates that the prosthetic leg 10 has been transitioned to a stair-ascending movement for ascending the staircase S (a stair-ascending mode). Accordingly, the control unit 17 outputs a signal to cause the rotating machine 124 to generate a rotational power required for ascending the staircase. Specifically, when a predetermined external force acting in the contraction direction is applied to the extension/contraction device 12 during the stair-ascending movement, the control unit 17 performs control such that the rotating machine 124 generates a rotational power acting in a direction, the rotational power being converted by the conversion unit 122, which is composed of the outer cylinder 126 and the spindle 127, into translational motion in an extension direction.

Following the contact of the prosthetic leg 10 with a step above the normal foot, when the wearer braces the prosthetic leg 10 via his/her femoral region for ascending the staircase, an external force acting in the contraction direction is applied to the extension/contraction device 12. The external force applied at this time is less intense than that applied to the extension/contraction device 12 in the stance phase, and is a force (load) less intense than the rotational torque of the rotating machine 124. Therefore, the rotary unit 121 rotates the spindle 127 coupled to the second engagement element 123b in the forward direction. As a result, as illustrated in FIG. 6, the outer cylinder 126 moves axially upward, whereby the extension/contraction device 12 extends.

The extension of the extension/contraction device 12 causes the above-knee member 2 coupled to the outer cylinder 126 via the arm part 22 to pivot forward (in the clockwise direction) around the pivot shaft 31 of the knee joint mechanism 3. Consequently, the prosthetic leg 10 causes the socket 5 coupled to the above-knee member 2 to move obliquely forward, and straightens the knee while raising the wearer's body as illustrated in FIG. 7, thereby returns to the standing position illustrated in FIG. 1. Thereafter, the above-described movements are repeated, so that he/she is allowed to ascend the staircase S using the prosthetic leg 10. With the prosthetic leg 10 of the present embodiment, the wearer can ascend the staircase S with a nearly natural gait because the wearer can perform the stair-ascending movement by applying a load to the prosthetic leg 10 by bracing the prosthetic leg 10 in contact with an upper step, while moving upward his/her body.

Other Embodiments

In the embodiment described above, the knee joint mechanism 3 has the rotary damper 32. However, the rotary damper 32 does not necessarily have to be provided. In the case of omitting the rotary damper 32, when the yielding movement is performed, the control unit 17 controls and causes the rotating machine 124 to generate such a rotational power that does not extend the extension/contraction device 12, so that the rotational power of the rotating machine 124 resists the backward rotation of the spindle 127 to the same or similar extent that the rotary damper 32 does.

In the embodiment described above, the transfemoral prosthesis 10 has been described as an example. However, the joint device of the present invention may be configured as a prosthetic arm. Further, the joint device of the present invention is applicable to a wide range of other joint devices having a configuration in which a linking unit links two members with each other such that the two members are movable relative to each other.

EXPLANATION OF REFERENCE NUMERALS

1: Below-Knee Member (First Member)
12: Extension/Contraction Device
121: Rotary Unit
122: Conversion Unit
123: Clutch Unit (Connection/Disconnection Unit)
123a: First Engagement Element (First Connection/Disconnection Member)
123b: Second Engagement Element (Second Connection/Disconnection Member)
124: Rotating machine
125: Transmission
128: Spring (First Urging part, Second Urging Part)
13: Battery
14: Six-Axis Force Sensor (First Acquisition Unit.)
15: Six-Axis Motion Sensor (Second Acquisition Unit)
16: Knee Joint Angle Sensor (Third Acquisition Unit)
17: Control Unit
2: Above-Knee Member (Second Member)
3: Knee Joint Mechanism (Linking Unit)
32: Rotary Damper (Adjustment Unit)
10: Prosthetic Leg (Joint Device)

The invention claimed is:

1. A joint device comprising
a linking unit that links a first member with a second member such that the first and second members are movable relative to each other; and
an extension/contraction device that is connected between the first member and the second member in a manner allowing power transmission, and is capable of varying an angle formed by the first member and the second member around the linking unit by extending and contracting,
wherein the extension/contraction device includes a rotary unit that is configured to generate a rotational power, and a conversion unit that is connected to the rotary unit in a manner allowing power transmission and is configured to convert the rotational power generated by the rotary unit into translational motion in an extension/contraction direction, and includes, between the rotary unit and the conversion unit, a connection/disconnection unit that is capable of connecting and disconnecting power transmission from the rotary unit to the conversion unit, and
wherein the connection/disconnection unit includes a first connection/disconnection member coupled to a side of the rotary unit and a second connection/disconnection member coupled to a side of the conversion unit, and further includes a first urging part that is configured to contract in an axial direction between the first connection/disconnection member and the second connection/disconnection member, and apply an urging force in a direction in which the first and second connection/disconnection members are constantly spaced apart from each other.

2. The joint device according to claim 1,
wherein the rotary unit includes a rotating machine that generates a rotational power upon supply of electric power.

3. The joint device according to claim 2, further comprising:
a control unit that controls the rotational power of the rotating machine.

4. The joint device according to claim 3,
wherein the control unit is configured to control the rotating machine such that when an external force acting in a contraction direction is applied to the extension/contraction device, the rotating machine generates a rotational power acting in a direction, the rotational power being converted by the conversion unit into translational motion in an extension direction of the extension/contraction device.

5. The joint device according to claim 1,
wherein in a state where the joint device is attached to a wearer's body such that the first member is positioned toward a distal end and is more distant than the second member from the wearer's body, the rotary unit is more distant than the conversion unit from the second member.

6. The joint device according to claim 1,
wherein the rotary unit includes a transmission.

7. The joint device according to claim 1, further comprising:
an adjustment unit that adjusts a movement of the linking unit.

8. The joint device according to claim 1, further comprising:
a first acquisition unit that acquires information regarding an external force acting in a contraction direction and applied to the extension/contraction device.

9. The joint device according to claim 1, further comprising:
a second acquisition unit that acquires information regarding an acceleration of the first member.

10. The joint device according to claim 1, further comprising:
a third acquisition unit that acquires information regarding the angle formed by the first member and the second member.

11. The joint device according to claim 1, further comprising:

a battery that supplies the rotary unit with electric power for generation of the rotational power.

12. The joint device according to claim 1, the joint device being attachable to a lower extremity of a wearer's body.

13. The joint device according to claim 12, the joint device being attachable to a part to serve as a knee joint of the lower extremity.

\* \* \* \* \*